US00PP31633P2

(12) United States Plant Patent
Olesen

(10) Patent No.: US PP31,633 P2
(45) Date of Patent: Apr. 7, 2020

(54) COMPACT FLORIBUNDA ROSE PLANT NAMED 'POULPAL074'

(50) Latin Name: ***Rosa* hybrid**
Varietal Denomination: Poulpal074

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,584

(22) Filed: Sep. 4, 2018

(51) Int. Cl.
*A01H 5/02* (2018.01)
*A01H 6/74* (2018.01)

(52) U.S. Cl.
USPC ..... Plt./146
CPC ..... *A01H 6/749* (2018.05)

(58) Field of Classification Search
USPC ..... Plt./146
See application file for complete search history.

(56) References Cited

PUBLICATIONS

"Venaria" downloaded from www.poulsenroser.com/assortment/rose-collections/palace/venaria.aspx on Jun. 6, 2019, 2 pages.*
UPOV hit on compact floribunda rose plant named 'Poulpal0747', QZ PBR 20172258, filed Sep. 19, 2017.*

* cited by examiner

*Primary Examiner* — Anne Marie Grunberg

(57) ABSTRACT

A new garden rose plant of the Compact Floribunda class which has abundant, orange flowers and attractive foliage. This new and distinct variety has shown to be uniform and stable in the resulting generations from asexual propagation.

1 Drawing Sheet

Botanical designation: *Rosa* hybrid.
Variety denomination: 'Poulpal074'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpal074', originated as a single seedling from the stated cross.

The new variety may be distinguished from its male pollen parent and female seed parent primarily by the following characteristics. The male pollen parent plant has apricot blend flowers while the new variety has orange flowers. The female seed parent plant has orange red flowers while the new variety has orange flowers.

The objective of the hybridization of this rose variety was to create a new and distinct variety with unique qualities, such as:

1. Uniform and abundant orange flowers;
2. Vigorous, but compact growth when propagated on its own roots;
3. Exceptional disease resistance.

This combination of qualities is not present in previously available commercial cultivars of this type, known to the inventor, and distinguish 'Poulpal074' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpal074' was selected in the spring of 2008 by the inventor as a single plant from the progeny of the aforementioned hybridization.

Asexual reproduction of 'Poulpal074' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpal074' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal074'. Specifically illustrated in the drawing is an open flower viewed from the side and above, flower petals detached, a cluster of flower buds, one of which has sepals removed showing reproductive flower parts, leaves and stems. Plants shown are 2 years of age.

DETAILED DESCRIPTION OF THE VARIETY

The following is a description of 'Poulpal074', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulac014', U.S. Plant Pat. No. 15,895 are compared to 'Poulpal074' in Chart 1.

CHART 1

| | 'Poulpal074' | 'Poulac014' |
|---|---|---|
| Petal Count | 40 | 30-35 |
| Flower Diameter | 80 mm | 60-65 mm |
| General Tonality of Flower Color | Orange Group 24B | Orange Group 25B with intonations of Orange-Red Group 33B to 33C |

FLOWER AND FLOWER BUD

Blooming habit: Continuous.

Flower bud:

*Size.*—Upon opening, 24 mm in length from base of receptacle to end of bud. Bud diameter is 13 mm.

*Bud form.*—Ovoid with broad base.

*Bud color.*—As sepals divide petals are Red Group 46A and Yellow Group 8C. Other intonations of Orange-Red Group 32B.

*Sepal inner surface.*—Color: Yellow-Green Group 145B with intonations of Greyed-Purple Group 186A. Surface: Lightly pubescent.

*Sepal outer surface.*—Color: Yellow-Green Group 144A with light intonations of Greyed-Purple Group 184A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—25 mm long, 7 mm wide.

*Receptacle.*—Texture: Smooth. Size: 8 mm in height, 7 mm wide. Color: Yellow-Green Group 144A with intonations of Greyed-Purple Group 184B. Shape: Campanulate.

*Pedicel.*—Surface: Smooth. Length: 35 mm. Diameter: 3 mm on average. Color: Yellow-Green Group 144C with intonations of Greyed-Purple Group 184B. Strength: Strong.

Flower bud development: Flower buds are borne in clusters of an average of 3 flower buds per stem.

Flower bloom:

*Fragrance.*—Moderate floral.

*Duration.*—The blooms have a duration on the plant of approximately 10 days. Petals fall cleanly away from plant after flowers have fully matured.

*Size.*—Flower diameter is 80 mm when open. Flower depth is 35 mm.

*Flower shape.*—Rosette, double, with many slightly overlapping petals of different sizes.

*Shape of flower, side view.*—The upper portion is flat. The lower portion is a flattened concave.

Petalage: Under normal conditions, flowers have about 40 petals.

General tonality of flower: Open flowers are Orange Group 24B.

Petal color:

*Outer petals.*—Upper surface: At the basal zone Yellow Group 12A. At the middle zone Yellow Orange 22C. At the marginal zone Red Group 39C. Lower surface: At the basal zone Yellow Group 8A. Middle zone Yellow-Orange Group 22B. Marginal zone Red Group 37C with occasional intonations of Red Group 39B.

*Inner petals.*—Upper surface: Orange Group 24B with streaks of Yellow Group 8A. Lower surface: Orange Group 24B with streaks of Yellow Group 8A.

Petals:

*Petal reflex.*—Inner and outer petals show very little or no reflex.

*Margin.*—Entire and uniform. Moderate undulations.

*Shape.*—Broad and elliptic. Apex shape: Rounded. Base shape: Acute.

*Size.*—41 mm (l)×38 mm (w).

*Texture.*—Smooth.

*Thickness.*—Average.

Petaloids:

*Size.*—30 mm (l) by 23 mm (w).

*Quantity:* 7 to 10.

*Shape.*—Elliptical with an acute base and rounded apices.

*Color.*—Orange Group 24B with streaks of Yellow Group 8A on both the upper and lower surfaces.

Reproductive flower parts:

*Pollen.*—None observed.

*Anthers.*—Size: 2 mm in length. Color: Greyed-Orange Group 163A. Quantity: 55 on average.

*Filaments.*—Color: Greyed-Orange Group N163A. Length: 7 mm.

*Pistils.*—Length: 6 mm. Quantity: 30 on average.

*Stigmas.*—Color: Greyed-Yellow Group 162A.

*Styles.*—Color: Green-White Group 157A.

*Location of stigmas.*—Inferior in location relative to the length of the filaments and the height of the anthers.

*Hips.*—None Observed.

PLANT

Plant growth: Upright, bushy. Plants are 45 to 55 cm in height, and 45 cm wide.

Stems:

*Color of juvenile growth.*—Yellow-Green Group 146D with intonations of Greyed-Red Group 182A.

*Color of mature growth.*—Yellow-Green Group 146C.

*Length.*—Canes are about 15 cm from the base of the plant to the flowering portion.

*Diameter.*—About 9 mm.

*Internodes.*—On mature canes about 42 mm between nodes.

*Surface texture.*—Young wood: Smooth. Older wood: Rough with small prickles.

Long prickles:

*Incidence.*—4 prickles per 10 cm of stem.

*Size.*—Average length of prickles on mature stems is 6 mm.

*Shape.*—Upper portion is linear. Lower portion is concave.

*Color.*—Juvenile prickles: Greyed-Red Group 180A. Mature prickles: Greyed-Red Group 180A.

Plant foliage:

*Compound leaf.*—120 mm (l)×100 (w).

*Quantity.*—2 leaves per 10 cm of stem on average.

*Leaf bearing angle to the stem.*—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 147C.

Plant leaves and leaflets:

*Stipules*.—Size: 22 mm long, 4 mm wide. Quantity: 2 per compound leaf. Shape: Linear, slightly broad based with outward extending apices. Margins: Finely serrated. Color:

*Petiole*.—Length: 30 mm. Diameter: 2 mm. Upper surface color: Yellow-Green Group 144A. Lower surface color: Yellow-Green Group 146D.

*Rachis*.—Length: 35 mm. Upper surface color: Yellow-Green Group 144A. Lower surface color: Yellow-Green Group 146D.

*Leaflet*.—Quantity: Normally 5 leaflets. Margins: Serrated. Size: Terminal leaflets are about 53 mm long, 35 mm wide. Shape: Generally elliptical. Base: Rounded. Apex: Mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Compact Floribunda rose class named 'Poulpal074', substantially as illustrated and described herein, due to its abundant orange flowers, disease resistance, and extended period of bloom.

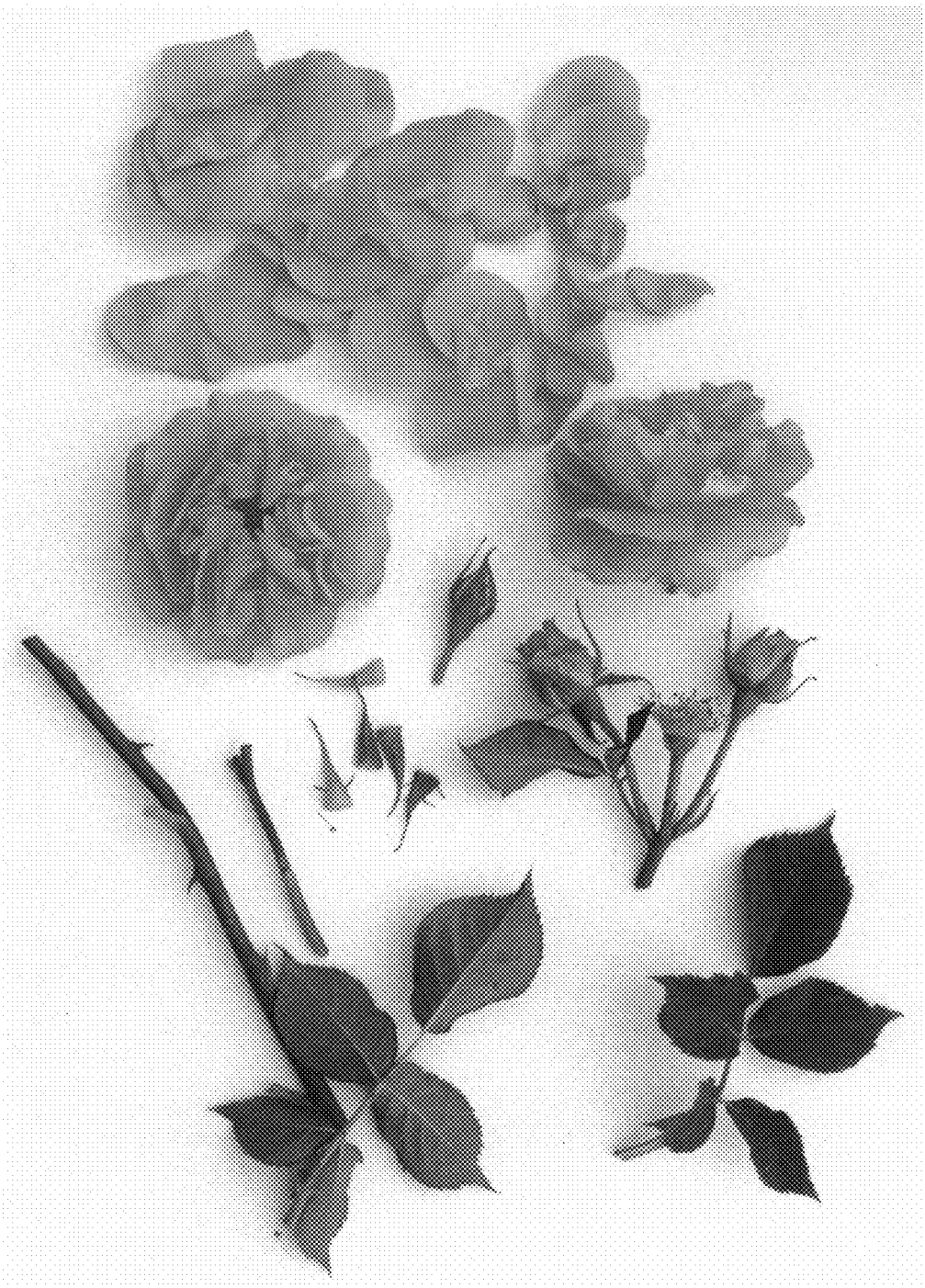

* * * * *